United States Patent [19]

Jee

[11] Patent Number: 5,604,259
[45] Date of Patent: Feb. 18, 1997

[54] TREATMENT OF BONE LOSS WITH IBUPROFEN OR FLURBIPROFEN

[75] Inventor: Webster S. S. Jee, Salt Lake City, Utah

[73] Assignee: University of Utah Research Foundation, Salt Lake City, Utah

[21] Appl. No.: 590,723

[22] Filed: Jan. 24, 1996

Related U.S. Application Data

[63] Continuation of Ser. No. 298,232, Aug. 30, 1994, abandoned, which is a continuation of Ser. No. 140,691, Oct. 21, 1993, abandoned, which is a continuation of Ser. No. 995,305, Dec. 22, 1992, abandoned, which is a continuation of Ser. No. 890,349, May 22, 1992, abandoned, which is a continuation of Ser. No. 733,366, Jul. 19, 1991, abandoned, which is a continuation of Ser. No. 644,871, Jan. 23, 1991, abandoned, which is a continuation of Ser. No. 541,456, Jun. 22, 1990, abandoned, which is a continuation of Ser. No. 372,220, Jun. 23, 1989, abandoned, which is a continuation of Ser. No. 223,575, Jul. 25, 1988, abandoned, which is a continuation of Ser. No. 872,045, Jun. 6, 1986, abandoned, which is a continuation-in-part of Ser. No. 824,072, Jan. 30, 1986, abandoned.

[51] Int. Cl.⁶ ..................................................... A61K 31/19
[52] U.S. Cl. ........................... 514/570; 514/568; 514/569
[58] Field of Search ..................................... 514/570, 568, 514/569

[56] References Cited

U.S. PATENT DOCUMENTS

| | | | |
|---|---|---|---|
| 4,101,668 | 7/1978 | Samour et al. | 424/275 |
| 4,486,436 | 12/1984 | Sunshine et al. | 424/263 |
| 4,677,132 | 6/1987 | Hayward | 514/411 |
| 5,190,981 | 3/1993 | Wechter | 514/900 |

FOREIGN PATENT DOCUMENTS

| | | |
|---|---|---|
| 68563 | 6/1982 | European Pat. Off. . |
| 137668 | 4/1985 | European Pat. Off. . |

OTHER PUBLICATIONS

A. W. Samuel, et al., Br. J. Surgery, vol. 66, No. 12, p. 901 (1979)(abstr. 106).
J. J. Lasfargues, et al., J. Periodontal Res. 18, 110–117 (1982).
R. S. Feldman, et al., J. Clin. Periodontal, 10, 131–136 (1983).
S. Nyman, et al., J. Periodontal, 50, 450–461 (1979).
A. H. Reddi, *Current Advances in Skeletongenesis* (M. Silberman and H. C. Salvkin, eds.), Excerpta Medica, Amsterdam–Oxford–Princeton, 77–86 (1982).
M. Torbinejad, et al., Calcif. Tissue Int. 29, 207–214 (1979).
I. M. Waite, et al., J. Periodontal Res. 16, 100–108 (1981).
M. Weaks–Dybvig, et al., J. Periodontal Res. 17, 90–100 (1982).
R. C. Williams, et al., J. Periodontal Res. 16, 659–665 (1981).
R. C. Williams, et al., Science 227, 640–642 (1985).

*Primary Examiner*—Theodore J. Criares
*Attorney, Agent, or Firm*—Thorpe, North & Western, L.L.P.

[57] ABSTRACT

This invention relates to the use of flurbiprofen and ibuprofen, their pharmaceutically acceptable salts and esters in a method of increasing bone mass and the treatment and prevention of bone mass loss excepting alveolar bone mass loss or increase. More particularly this invention relates to the treatment of osteoporosis by administering flurbiprofen or ibuprofen, their salts or esters.

6 Claims, No Drawings

TREATMENT OF BONE LOSS WITH IBUPROFEN OR FLURBIPROFEN

CROSS REFERENCE TO RELATED APPLICATIONS

This application is a continuation of U.S. application Ser. No. 08/298,232, filed Aug. 30, 1994, now abandoned, which is a continuation of U.S. Ser. No. 08/140,691 filed Oct. 21, 1993, now abandoned, which is a continuation of U.S. Ser. No. 07/995,305 filed Dec. 22, 1992, which is a continuation of U.S. Ser. No. 07/890,349 filed May 22, 1992, now abandoned, which is a continuation of U.S. Ser. No. 07/733,366 filed Jul. 19, 1991, now abandoned, which is a continuation of U.S. Ser. No. 07/644,871 filed Jan. 23, 1991, now abandoned, which is a continuation of U.S. Ser. No. 07/541,456 filed Jun. 22, 1990, now abandoned, which is a continuation of U.S. Ser. No. 07/372,220 filed Jun. 23, 1989, now abandoned, which is a continuation of U.S. Ser. No. 07/223,575 filed Jul. 25, 1988, now abandoned, which is a continuation of U.S. Ser. No. 06/872,045 filed Jun. 6, 1986, now abandoned, which is a continuation-in-part of U.S. Ser. No. 06/824,072 filed Jan. 30, 1986, now abandoned, of Webster S. S. Jee for TREATMENT OF BONE LOSS.

FIELD OF INVENTION

This invention relates to a method of decelerating bone resorption and enhancing bone formation, excepting alveolar bone, in mammals by administering flurbiprofen or ibuprofen or salts or esters thereof.

BACKGROUND OF INVENTION

Osteoporosis is a well known condition which results from decreased bone mass involving a process of loss of both bone mineral and protein matrix components. This disease condition occurs in a number of situations, and most commonly in situations where there is an estrogen deficit, such as, in postmenopausal women; situations involving an excess of catabolic hormone such as is found in Cushing's disease; in situations involving long term administration of corticosteroids; and in situations where a patient is immobilized. Osteoporosis is also known to occur in certain patients with liver disease, gonadal dysgenesis, and osteogenesis imperfecta, which is an inherited condition in which the bones are abnormally brittle and subject to fractures. Osteoporosis can be detected by overt signs or by X-ray examination. Overt indicators include pain in the weight-bearing vertebrae, local tenderness and pain if a fracture has occurred, loss in height, and an increase in calcium levels in the urine which eventually decline as bone calcium resevoirs are depleted.

Current methods of treatment include exercise, providing the patient with physical support to reduce the weight stress on the skeletal structure, estrogen therapy, particularly for postmenopausal women, and consumption of calcium or calcium containing substances such as milk. Except in situations where Cushing's disease has been successfully treated none of the current methods of treating osteoporosis results in restoration of bone mass. The invention described and claimed herein provides for a method of treating demineralized bone conditions whereby there is a restoration of the bone mass. Bone cells are of two types: osteoblasts which are associated with bone production; and osteoclasts which are associated with bone absorption and removal. It is believed that the compounds employed in the present invention decrease the number of osteoclasts and stimulate the metabolic activity of the osteoblasts, and/or increase the size of the osteoblasts. Nevertheless, that the compounds employed in the present invention are having an effect on the osteoclast activity is not being ruled out. As will become apparent from the information provided below a surprising aspect of this invention is the dosage at which the compounds are effective in increasing bone mass.

PRIOR ART

Flurbiprofen and ibuprofen are non-steroidal antiinflammatory agent when administered at the appropriate dose. Certain nonsteroidal antiinflammatory agents including flurbiprofen and ibuprofen are known to have an effect on alveolar bone resorption. R. C. Williams, et al., Science 227, 640–642 (1985) reports the effect of flurbiprofen on alveolar bone resorption in the beagle dog. In J. Periodontal Res. 16, 659–655 (1981) R. C. Williams, et al., have demonstrated in beagle dogs that tetracycline administration is effective over a 12-month period in decreasing the rate of alveolar bone loss. The results of a retrospective study reported by R. S. Feldman, et al., in J. Clin. Peridontal. 10, 131–136 (1983) suggest that the chronic ingestion of aspirin or aspirin together with indomethacin resulted in the inhibition of alveolar bone loss. Other references which report the effect of indomethacin on bone resorption associated with peridontal disease include M. Weaks-Dybvig, et al., J. of Periodontal Research 17, 90–100 (1982); S. Nyman, et al., J. Periodontol. 50, 450–461 (1979); and J. J. Lasfargues, et al., J. of Periodontal Research 16, 110–117 (1983). I. M. Waite, et al., J. of Periodontal Research 16, 100–108 (1981), reports the periodontal status of subjects receiving nonsteroidal antiinflammatory drugs. There are described in European patent application EP 068,563 compounds which modify the balance between bone production and bone resorption. Also, U.S. Pat. No. 4,101,668 disclosed compounds which are useful in modifying the balance between the rate of bone resorption and the rate of bone deposition in a host animal. M. Torbinejad, et al., Calcif. Tissue Int. 29, 207–214 (1979) reports that bone resorption, induced by injection via the root canal of simulated immune complexes into the periapical tissues of cat maxillary cuspids, was blocked by the systemic administration of indomethacin.

A. H. Reddi provides a review of the formation and remodeling of endochondral bone in "Local and Systemic Mechanisms Regulating Bone Formation and Remodeling: An Overview", 77–86, *Current Advances In Skeletogenesis*, ed. M. Silbermann and H. C. Slavkin, Excerpta Medica, Amsterdam-Oxford-Princeton, 1982.

SUMMARY OF INVENTION

The present invention provides a method for increasing bone mass. This invention is of particular use in pediatric patents with inadequate bone mass and subject to increased risk to osteoporosis and in patients having a demineralized bone condition. This invention also provides a method for preventing bone mass loss which is of particular use in a patient susceptible to a demineralized bone condition. By demineralized bone condition is meant a situation wherein a patient's bone mineral stores, primarily calcium stores, are undergoing depletion such that there is a net loss in mineral and ultimately bone mass. This invention further provides a method for preventing or treating osteoporosis in a patient in need of such treatment. This invention additionally provides a pharmaceutical composition in unit dosage form useful in treating or preventing bone mass loss. The methods and composition of the present invention utilize as the active ingredient flurbiprofen or ibuprofen and pharmaceutically acceptable salts and lower alkly esters thereof and isomers thereof. Flurbiprofen is known chemically as 2-fluoro-alphamethyl[1,1'-biphenyl]-4-acetic acid. Ibuprofen is known chemically as α-methyl-4-(2-methylpropyl)benzeneacetic acid. Lower alkyl esters includes esters having from 1 to 6 carbon atoms, such as, methyl, ethyl, propyl, butyl, pentyl, and hexyl and branched forms thereof, such as, isopropyl, tert-butyl, isobutyl, etc. Pharmaceutically acceptable salts of flurbiprofen and ibuprofen useful in practicing the present invention include aluminum salts, alkali metal salts such as potassium and sodium salts, alkaline earth salts such as calcium or magnesium, or amine salts such as tert-butyl amine, ethyl amine, triethanolamine, etc.

DETAILED DESCRIPTION OF INVENTION

Flurbiprofen and ibuprofen are is described in U.S. Pat. Nos. 3,755,427 and 3,228,831, respectively. The structures of flurbiprofen and ibuprofen are set forth herein in the Formula Chart following the Examples. Esters and salts of flurbiprofen and ibuprofen utilized in practicing the present invention are prepared by means well known in the art. Aluminum salts are prepared for example as generally described in U.S. Pat. Nos. 4,361,580 and 4,145,440.

In practicing the present invention the patient to be treated is any mammal in need of treatment. Illustratively, mammals such as members of the equine, bovine, porcine, canine, and feline family of animals, rats, mice, rabbits, sheep, and higher mammals such as monkeys and humans displaying overt signs of bone deterioration or expected to be in need of treatment. The largest population of patient to be treated will be the postmenopausal female and older patients who are bedridden or otherwise immobilized. Also patients on long term corticosteroid therapy will make up a significant part of the population to benefit from the invention described herein. Any mammal undergoing or anticipated to be susceptible to bone loss due to demineralization of the bone will benefit from the present invention. The type of bone targeted for treatment by the present invention is endochondral bone, i.e., long bones, vertebrae, and other bones forming the basic skeletal frame, as well as bones of the feet and hands or paws as the case may be.

It is believed that the compounds utilized in the present invention have their effect through increasing the number of, the size of, and the metabolic activity of the osteoblasts. The compounds utilized herein appear to increase the overall metabolic activity of the osteoblasts resulting in bone formation. It was particularly surprising to find that the effect is seen with relatively low doses of the compound and is less effective as the dosage is increased as will be evident from the data provided herein.

Although flurbiprofen and ibuprofen, their salts, esters, and isomers as described herein are effective in practicing the present invention when administered subcutanenously or by injection the preferred route of administration is orally. Administration in the form of suppositories or implants for sustained release or topically is also effective in practicing the present invention. In essence any mode of administration which results in the therapeutic agent being incorporated into the blood stream including transdermal administration may be employed in practicing the invention as set forth herein. Suitable forms for oral administration include tablets, capsules, pills, powders, granules, solutions or suspensions. Sterile aqueous solutions or suspensions are also suitable for injection. Suitable topical forms of administration include gels, pastes, or an adhesive patch containing the active ingredient.

Compositions suitable for use in the present invention are formulated using conventional pharmaceutical carriers. For example, solid dosage forms typically will contain lubricants such as stearic acid or magnesium stearate and fillers such as lactose, sucrose, cornstarch, or perhaps disintegrating agents such as alginic acid. Injectable solutions or suspensions may contain sterile liquids such as water or oils with surfactants as needed. Sustained release formulations may be prepared as generally described in U.S. Pat. Nos. 4,389,393 and 3,065,143. Representative examples of compositions useful in practicing the present invention are set forth hereinbelow.

The quantity of flurbiprofen, pharmaceutically acceptable salt, ester, or isomer effective in treating, inhibiting, or preventing loss of bone mass resulting from demineralization of the bone, i.e., the amount of compound effective in practicing the invention described and claimed herein, varies from about 0.01 to 5.0 milligrams per kilogram per day. Thus the daily dose of flurbiprofen or a salt or ester or isomer thereof for an average weight (70 kg) human adult will vary from about one to about 350 milligrams per day.

The quantity of ibuprofen, pharmaceutically acceptable salt, ester, or isomer effective in treating, inhibiting, or preventing loss of bone mass resulting from demineralization of the bone, i.e., the amount of compound effective in practicing the invention described and claimed herein, varies from about 0.08 to 10 milligrams per kilogram per day, and preferably from about 0.4 to 5 milligrams per kilogram per day. Thus the daily dose of ibuprofen or a salt or ester thereof for an average weight (70 kg) human adult will vary from about 5.6 to 700 milligrams per day.

The utility of the present invention has been demonstrated in weanling rats which were administered 0, 0.02, 0.1, 0.5, and 2.5 mg/kg of flurbiprofen orally once a day for 21 days. A 2×3 mm area of the secondary spongiosa of the proximal tibia was measured with the aid of microradiographs and the Quantmet 720 with the following results:

| Flurbiprofen (mg/kg) | Proximal tibial metaphysis area (mm$^2$) |
| --- | --- |
| 0 | 0.69 ± 0.06 |
| 0.02 | 0.81 ± 0.11 |
| 0.10 | 0.84 ± 0.07 P < 0.01 |
| 0.50 | 0.86 ± 0.07 P < 0.01 |
| 2.50 | 0.80 ± 0.07 P < 0.05 |

A summary of the significant changes in percent of the other measured marameters of the proximal tibial metaphysis and the tibial shaft compared to controls was as follows:

| SUMMARY OF FLURBIPROFEN EXPERIMENT (Significant changes, $P < 0.05$) | | | | |
| --- | --- | --- | --- | --- |
| Dose (mg/kg/day) | 0.02 | 0.10 | 0.50 | 2/50 |
| Longitudinal growth rate | 0 | ↑23% | ↑24% | 0 |
| Thickness of growth plate | 0 | ↑29% | ↑27% | 0 |
| Size of degenerative cells | 0 | 0 | 0 | 0 |
| Production rate of cell | 0 | 0 | 0 | 0 |
| Metaphysis | | | | |
| Area | 0 | ↑21% | ↑23% | ↑15% |
| Perimeter | 0 | ↑23% | ↑27% | 0 |
| P/A | 0 | 0 | 0 | 0 |

-continued

SUMMARY OF FLURBIPROFEN EXPERIMENT (Significant changes, P < 0.05)

| Dose (mg/kg/day) | 0.02 | 0.10 | 0.50 | 2/50 |
|---|---|---|---|---|
| S/V | 0 | 0 | 0 | 0 |
| Fraction area | 0 | ↑21% | ↑23% | ↑15% |
| Cortex | | | | |
| Total area (AT) | 0 | ↑7% | ↑8% | 0 |
| Cortical area (AC) | 0 | ↑11% | ↑12% | 0 |
| Marrow area (AM) | 0 | 0 | 0 | 0 |
| Periosteal perimeter | 0 | ↑4% | ↑5% | 0 |
| Endosteal perimeter | 0 | 0 | 0 | 0 |
| AC/AT | 0 | 0 | 0 | 0 |
| Resorption rate | 0 | 0 | 0 | 0 |
| Periosteum formation rate | 0 | ↑39% | ↑40% | 0 |
| Appositional rate | ↑19% | ↑32% | ↑35% | 0 |
| Label length | 0 | 0 | 0 | 0 |
| Endosteum formation rate | 0 | 0 | 0 | 0 |
| Appositional rate | 0 | 0 | 0 | 0 |
| Label length | 0 | 0 | 0 | 0 |
| Cell Count | | | | |
| Bone | ↑25% | ↑45% | ↑53% | ↑31% |
| Calc. cartilage | ↑48% | ↑78% | ↑74% | ↑19% |
| Hard tissue | ↑33% | ↑56% | ↑60% | ↑17% |
| No. of osteoblast (OB) | 0 | 0 | 0 | 0 |
| No. of osteoclast (OC) | ↓49% | ↓54% | ↓48% | ↓31% |
| OB/Perimeter | 0 | 0 | 0 | 0 |
| OC/Perimeter | ↓50% | ↓65% | ↓69% | ↓42% |
| OB/OC | ↑78% | ↑123% | ↑113% | ↑70% |
| Surface/Volume | — | ↓16% | — | — |

The following examples provide illustrative compositions useful in practicing the present invention. In each instance flurbiprofen has been used, although in each instance ibuprofen could be substituted therefor to give a composition useful in practicing the invention.

EXAMPLE 1

Hard Gelatin Capsules

One thousand two-piece hard gelatin capsules for oral use, each capsule containing 25 mg of flurbiprofen, are prepared from the following:

| | |
|---|---|
| Flurbiprofen | 25 gm |
| Lactose | 100 gm |
| Corn Starch | 20 gm |
| Talc | 20 gm |
| Magnesium stearate | 2 gm |

The flurbiprofen (finely divided by means of an air micronizer) is added to the other finely powdered ingredients, mixed thoroughly and then encapsulated in the usual manner.

EXAMPLE 2

Soft Gelatin Capsule

One piece soft gelatin capsules for oral use, each containing 25 mg of flurbiprofen (divided by means of an air micronizer), are prepared by first suspending the compound in 0.5 ml of corn oil to render the material capsulatable and then capsulating in the above manner.

EXAMPLE 3

Tablets

One thousand tablets, each containing 25 mg of flurbiprofen, are prepared from the following types and amounts of ingredients:

| | |
|---|---|
| Flurbiprofen micronized | 25 gm |
| Lactose | 75 gm |
| Corn Starch | 50 gm |
| Magnesium stearate | 4 gm |
| Light liquid petrolatum | 5 gm |

The flurbiprofen (finely divided by means of an air micronizer) is added to the other ingredients and thoroughly mixed and slugged. The slugs are broken down by forcing through a number sixteen screen. The resulting granules are then compressed into tablets each containing 25 mg of flurbiprofen.

EXAMPLE 4

Oral Suspension

One thousand ml of an aqueous suspension for oral use, containing in each teaspoonful (5 ml) dose, 50 mg of flurbiprofen sodium salt is prepared from the following types and amounts of ingredients:

| | |
|---|---|
| Flurbiprofen sodium salt micronized | 10 gm |
| Citric Acid | 2 gm |
| Benzoic Acid | 1 gm |
| Sucrose | 400 gm |
| Cellulose, microcrystalline | 10 gm |
| Lemon oil | 2 gm |
| Polysorbate 80 | 5 gm |
| Deionized water, qs | 1000 ml |

The citric acid, benzoic acid, sucrose, cellulose, lemon oil and polysorbate 80 are dispersed in sufficient water to make 850 ml of suspension. The flurbiprofen sodium salt (finely divided by means of an air micronizer) is stirred into the syrup until uniformly distributed. Sufficient water is added to make 1000 ml.

EXAMPLE 5

Sustained Release Tablet

The following formulation is representative of a 50 mg sustained release formulation useful in practicing the present invention. The 50 mg sustained release formulation may be used in place of other dosage unit forms which contain, e.g., 25 mg of active ingredient for administration twice a day.

| | | |
|---|---|---|
| (a) | Flurbiprofen milled | 50.0 mg |
| (b) | Lactose USP hydrous bolted | 95.0 mg |
| (c) | Pregelatinized starch NF | 10.5 mg |
| (d) | Purified water USP, q.s. | |
| (e) | Methocel K 15M premium | 95.0 mg |
| (f) | Colloidal silicon dioxide NF | 1.0 mg |
| (g) | Magnesium stearate NF | 2.5 mg |
| (h) | Hydroxypropyl methylcellulose 2910 UPS 15 CPS | 10.0 mg |
| (i) | Film coat concentrate white FC-100-PC | 2.0 mg |
| (j) | Purified water USP, q.s. ad | |

Ingredients (a) to (d) are blended, granulated, wet screened, and dried, then mixed with ingredients (e) to (g) and coated with ingredients (h) to (j).

EXAMPLE 6

Tablet

For a tablet to be administered once per day 50 mg of flurbiprofen is combined with the following excipients to provide release of active ingredient over a twenty-four hour period:

22.7 mg of hydroxypropyl methylcellulose 2208 USP, 15000 cps 0.5 mg of colloidal silicon dioxide NF 2.5 mg of magnesium stearate NF, powder food grade The foregoing examples are merely illustrative of pharmaceutical formulations which are useful in practicing the present invention.

Formula Chart

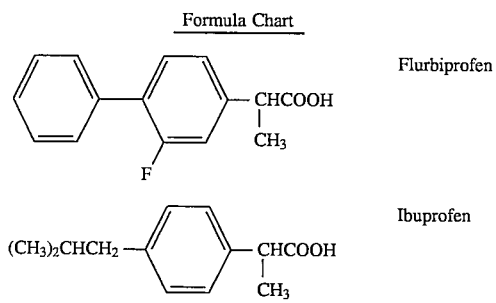

We claim:

1. A method of increasing bone mass, excepting alveolar bone mass, in a patient in need thereof which comprises administering to said patient an effective amount of flurbiprofen or ibuprofen or a pharmaceutically acceptable salt or lower alkyl ester thereof.

2. The method of claim 1 wherein the patient has a demineralized bone condition.

3. A method of treating bone mass loss, excepting alveolar bone mass loss, in a patient in need thereof which comprises administering to said patient an effective amount of flurbiprofen or ibuprofen or a pharmaceutically acceptable salt or lower alkyl ester thereof.

4. The method of claim 3 wherein the patient has a demineralized bone condition.

5. A method for treating osteoporosis in a patient in need thereof which comprises administering to said patient an effective amount of flurbiprofen or ibuprofen or a pharmaceutically acceptable salt or lower alkyl ester thereof.

6. The method of claim 5 wherein the patient to be treated is a post-menopausal human.

* * * * *